(12) United States Patent
Yan et al.

(10) Patent No.: US 12,070,624 B2
(45) Date of Patent: Aug. 27, 2024

(54) VERIFICATION PHANTOM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Hao Yan, Xi'an (CN); Zhongya Wang, Xi'an (CN); Wen Wang, Xi'an (CN); Jiuliang Li, Xi'an (CN); Dong Liu, Xi'an (CN); Shan Chen, Xi'an (CN); Deping Chen, Xi'an (CN); Hui Liu, Xi'an (CN); Pengfei Zhang, Xi'an (CN); Daliang Li, Xi'an (CN); Jinsheng Li, Xi'an (CN)

(73) Assignees: OUR UNITED CORPORATION, Xi'an (CN); SHENZHEN OUR New MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 151 days.

(21) Appl. No.: 17/710,928

(22) Filed: Mar. 31, 2022

(65) Prior Publication Data
US 2022/0219018 A1    Jul. 14, 2022

Related U.S. Application Data

(63) Continuation-in-part of application No. 17/432,901, filed as application No. PCT/CN2019/075761 on Feb. 21, 2019, now Pat. No. 11,819,711.

(30) Foreign Application Priority Data

Mar. 31, 2021  (CN) .......................... 202110354072.6
Mar. 31, 2021  (CN) .......................... 202120664881.2

(Continued)

(51) Int. Cl.
*A61N 5/10* (2006.01)

(52) U.S. Cl.
CPC .... *A61N 5/1075* (2013.01); *A61N 2005/1076* (2013.01)

(58) Field of Classification Search
CPC ...................... A61N 2005/1076; A61N 5/1075
See application file for complete search history.

(56) References Cited

U.S. PATENT DOCUMENTS

2003/0231740 A1* 12/2003 Paliwal ............... A61N 5/1048
378/167
2004/0120560 A1    6/2004 Robar et al.
(Continued)

FOREIGN PATENT DOCUMENTS

CN        200951265 Y      9/2007
CN        201936015 U      8/2011
(Continued)

OTHER PUBLICATIONS

Notice of allowance of U.S. Appl. No. 17/432,901 dated Jul. 13, 2023.
(Continued)

*Primary Examiner* — Blake C Riddick
(74) *Attorney, Agent, or Firm* — Knobbe, Martens, Olson & Bear, LLP

(57) ABSTRACT

Provided is a verification phantom. The verification phantom is provided with a slot for holding a film, wherein the slot includes a first slot and a second slot; an opening of the first slot and an opening of the second slot are both disposed on a first outer surface of the verification phantom; and an extraction groove is disposed at a junction, on the first outer surface, of the opening of the first slot and the opening of the second slot.

20 Claims, 10 Drawing Sheets

(30) Foreign Application Priority Data

Mar. 31, 2021 (CN) .................... 202120665447.6
Mar. 31, 2021 (CN) .................... 202120677566.3

(56) References Cited

U.S. PATENT DOCUMENTS

| | | | |
|---|---|---|---|
| 2005/0013406 A1* | 1/2005 | Dyk | A61N 5/1049 |
| | | | 378/65 |
| 2005/0259793 A1* | 11/2005 | Yeo | A61N 5/1048 |
| | | | 378/182 |
| 2006/0002519 A1 | 1/2006 | Jenkins et al. | |
| 2006/0203967 A1 | 9/2006 | Nilsson | |
| 2007/0165779 A1 | 7/2007 | Chen et al. | |
| 2008/0219410 A1 | 9/2008 | Gunzert-Marx et al. | |
| 2010/0288916 A1* | 11/2010 | Cho | G01D 15/00 |
| | | | 378/207 |
| 2012/0230462 A1 | 9/2012 | Robar et al. | |
| 2013/0006035 A1* | 1/2013 | Aitkenhead | A61N 5/1071 |
| | | | 378/207 |
| 2015/0085993 A1 | 3/2015 | Scheib | |
| 2015/0139513 A1 | 5/2015 | Niu et al. | |
| 2017/0050052 A1 | 2/2017 | Burgett et al. | |
| 2018/0339173 A1 | 11/2018 | Kilby et al. | |
| 2019/0001156 A1 | 1/2019 | Tulik et al. | |
| 2019/0175951 A1 | 6/2019 | Yu et al. | |
| 2019/0329072 A1 | 10/2019 | Magro et al. | |
| 2020/0061392 A1 | 2/2020 | Filiberti et al. | |
| 2020/0129785 A1 | 4/2020 | Li et al. | |
| 2020/0179723 A1* | 6/2020 | Gagneur | A61N 5/1075 |
| 2020/0289850 A1 | 9/2020 | Wösle | |
| 2020/0315567 A1* | 10/2020 | Constantin | A61N 5/1075 |
| 2020/0346042 A1 | 11/2020 | Maltz | |
| 2020/0359988 A1 | 11/2020 | Woods et al. | |
| 2020/0368551 A1 | 11/2020 | Bassalow et al. | |
| 2021/0128951 A1 | 5/2021 | Mead et al. | |
| 2022/0203131 A1 | 6/2022 | Wang et al. | |

FOREIGN PATENT DOCUMENTS

| | | |
|---|---|---|
| CN | 203138520 U | 8/2013 |
| CN | 103353602 A | 10/2013 |
| CN | 203483752 U | 3/2014 |
| CN | 203525145 U | 4/2014 |
| CN | 203802968 U | 9/2014 |
| CN | 104415459 A | 3/2015 |
| CN | 105233427 A | 1/2016 |
| CN | 205460526 U | 8/2016 |
| CN | 105983182 A | 10/2016 |
| CN | 206252739 U | 6/2017 |
| CN | 206381505 U | 8/2017 |
| CN | 108525140 A | 9/2018 |
| CN | 108853758 A | 11/2018 |
| CN | 208243929 U | 12/2018 |
| CN | 208405799 U | 1/2019 |
| CN | 109350865 A | 2/2019 |
| CN | 111588996 A | 8/2020 |
| CN | 211584937 U | 9/2020 |
| CN | 111836665 A | 10/2020 |
| CN | 112402817 A | 2/2021 |
| CN | 215741438 U | 2/2022 |
| EP | 1967231 A1 | 9/2008 |
| JP | 2011239830 A | 12/2011 |
| JP | 2016221156 A | 12/2016 |
| KR | 20100111985 A | 10/2010 |
| KR | 20120079726 A | 7/2012 |
| WO | 0061024 A1 | 10/2000 |
| WO | 2012053770 A2 | 4/2012 |

OTHER PUBLICATIONS

International search report of PCT application No. PCT/CN2019/075761 dated May 30, 2019.

First office action of Chinese application No. 202010398582.9 dated Aug. 18, 2021.

First office action of Chinese application No. 201980000893.0 dated Dec. 10, 2021.

China National Intellectual Property Administration, Notification to grant patent right for invention of Chinese application No. 201980000893.0 dated Jun. 21, 2022, which is foreign counterpart application of this US application.

Jia Weijuan et al., Simulator and Block Carriage Based Treatment Simulation Before Radiotherapy, Chinese Journal of Medical Physics, vol. 31. No.1, Jan. 31, 2014, entire document.

China National Intellectual Property Administration, First office action of Chinese application No. 202210842654.3 issued on Apr. 24, 2024.

China National Intellectual Property Administration, First Office action of Chinese application No. 202110354072.6 issued on Jun. 12, 2024, which is foreign counterpart application of this US application, 17 pages.

* cited by examiner

US 12,070,624 B2

VERIFICATION PHANTOM

CROSS-REFERENCE TO RELATED APPLICATIONS

This application is a continuation-in-part of U.S. application Ser. No. 17/432,901, filed on Aug. 20, 2021, which is a US national phase of International Application No. PCT/CN2019/075761, filed on Feb. 21, 2019, the disclosure of each of which is herein incorporated by reference in its entirety. This application claims priority to Chinese Patent Application No. 202120665447.6 filed on Mar. 31, 2021, Chinese Patent Application No. 202120677566.3 filed on Mar. 31, 2021, Chinese Patent Application No. 202110354072.6 filed on Mar. 31, 2021, and Chinese Patent Application No. 202120664881.2 filed on Mar. 31, 2021, the disclosure of each of which is herein incorporated by reference in its entirety.

TECHNICAL FIELD

The present disclosure relates to the field of radiotherapy technologies, and in particular, relates to a verification phantom.

BACKGROUND

A radiotherapy system may generally include: a rotating gantry and a treatment head disposed on the rotating gantry. Rays emitted from the treatment head can be used to treat a patient at a target point on an affected part. Under normal circumstances, a beam focus (i.e., an isocenter of treatment) of the rays emitted from the treatment head should be in coincidence with an isocenter of mechanical rotation of the rotating gantry. When the target point is positioned at a position of the isocenter of mechanical rotation, the beam focus can accurately irradiate the target point, thereby realizing precise treatment. However, due to installation errors and other reasons, there may be a deviation between the isocenter of treatment and the isocenter of mechanical rotation. Here, if the target point is positioned to the isocenter of mechanical rotation, the beam focus may not accurately irradiate the position of the target point, such that the precise treatment cannot be realized.

SUMMARY

The present disclosure provides a verification phantom. The technical solutions are as follows.

The verification phantom is provided with a slot for holding a film, wherein the slot includes a first slot and a second slot; an opening of the first slot and an opening of the second slot are both disposed on a first outer surface of the verification phantom; and an extraction groove is disposed at a junction, on the first outer surface, of the opening of the first slot and the opening of the second slot.

It should be understood that both the foregoing general description and the following detailed description are merely exemplary and explanatory, and are not intended to limit the present disclosure.

BRIEF DESCRIPTION OF THE DRAWINGS

To describe the technical solutions in the embodiments of the present disclosure more clearly, the following briefly introduces the accompanying drawings required for describing the embodiments. Apparently, the accompanying drawings in the following description show merely some embodiments of the present disclosure, and a person of ordinary skills in the art may still derive other drawings from these accompanying drawings without creative efforts.

The embodiments of the present disclosure have been illustrated explicitly through the drawings above, and will be described in more detail below. These drawings and text descriptions are not intended to limit the scope of the inventive conception in any way, but to explain the concept of the present disclosure to persons skilled in the art by referring to particular embodiments.

DETAILED DESCRIPTION

To present the objects, technical solutions and advantages of the present disclosure more clearly, the embodiments of the present disclosure will be described in further detail with reference to the accompanying drawings.

In the related art, in order to ensure the precision of radiotherapy, a verification phantom for verifying the deviation between an isocenter of treatment and an isocenter of mechanical rotation is provided, such as a MIMI phantom. Before the radiotherapy is performed, this verification phantom may be configured to verify whether the isocenter of treatment is in coincidence with the isocenter of mechanical rotation (that is, whether a deviation exists). When a deviation is present between the isocenter of treatment and the isocenter of mechanical rotation, the position of a treatment couch can be adjusted in time based on the deviation, thereby improving the coincidence precision between the isocenter of mechanical rotation and an isocenter of a device.

However, during usage of the above verification phantom, a film needs to be first inserted into a film cassette and then the film cassette with the film inserted needs to be placed into the verification phantom. Since the film cassette with the film inserted needs to be extracted from the verification phantom multiple times, abrasions may be present between the film cassette and the verification phantom after long-term use, which can affect the precision in detecting the deviation of the isocenter of treatment.

Figure 1:
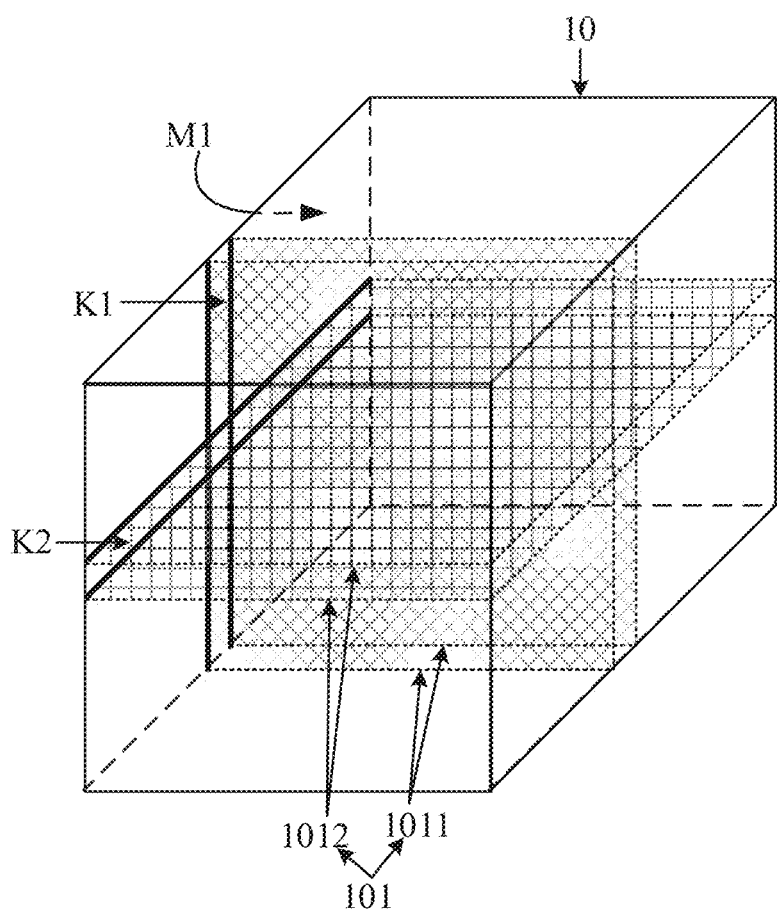
FIG. 1 is a schematic structural diagram of a verification phantom according to an embodiment of the present disclosure.
Figure 2:
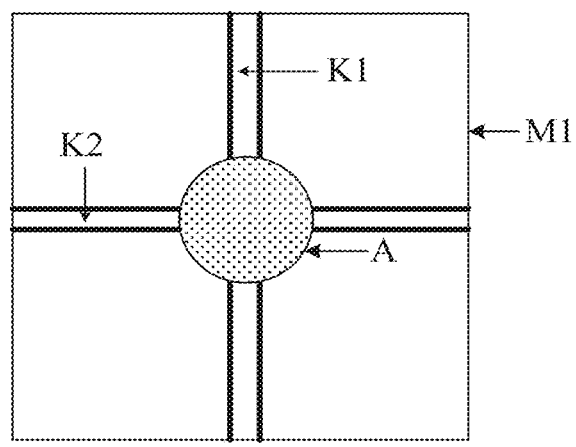
FIG. 2 is a side view of a verification phantom according to an embodiment of the present disclosure.

FIG. 1 is a schematic structural diagram of a verification phantom according to an embodiment of the present disclosure. FIG. 2 is a side view of a verification phantom according to an embodiment of the present disclosure. As shown in FIG. 1 and FIG. 2, the verification phantom 10 is provided with a slot 101 for holding a film. The slot 101 includes a first slot 1011 and a second slot 1012. An opening K1 of the first slot 1011 and an opening K2 of the second slot 1012 may be both disposed on a first outer surface M1 of the verification phantom 10. An extraction groove A may be disposed at a junction, on the first outer surface M1, of the opening K1 of the first slot 1011 and the opening K2 of the second slot 1012. The extraction groove A may be a groove near the intersection point of the two slots, and may be communicated with both the first slot 1011 and the second slot 1012.

Since the verification phantom 10 is provided with the slot 101 for holding the film, when the verification phantom 10 is used for verifying the deviation between the isocenter of treatment and the isocenter of mechanical rotation, the film only needs to be inserted into the two slots disposed on the first outer surface M1. In addition, since the extraction groove A separately communicated with the two slots is disposed on the first outer surface M1, a therapist can insert and extract the film more conveniently.

In a case that the verification phantom 10 is configured to verify the deviation between the isocenter of treatment and the isocenter of mechanical rotation, a film may be first inserted into the first slot 1011 through the opening K1 in the first outer surface M1; a center of the verification phantom 10 is aligned with a mechanical isocenter; then, the radiation source (an initial rotation angle of a gantry may be 0 degrees) irradiates the verification phantom 10, thereby forming a focal spot on the film inserted in the first slot 1011; a therapist takes out the film inserted in the first slot 1011, and then inserts another film into the second slot 1012 through the opening K2 in the first outer surface M1; the radiation source (the rotation angle of the gantry may be 90 degrees) irradiates the verification phantom 10, thereby forming a focal spot on the film inserted in the second slot 1012; and the therapist may take out the film inserted in the second slot 1012. The two films are scanned by the scanner to obtain two images containing focal spots. Afterwards, the therapist may further upload the two images containing the focal spots to the image server. Since the beam focus of the radiation source is theoretically in coincidence with the mechanical isocenter, the image server may analyze the two images containing the focal spots to obtain actual coordinates of the beam focus, and then determine a deviation of the isocenter of treatment from the isocenter of mechanical rotation based on the actual coordinates of the beam focus and coordinates of the mechanical isocenter. Afterwards, the image server may send the deviation to the control host, such that the control host adjusts the position of the treatment couch based on the deviation. In addition, the control host may also store the deviation, and precisely position a patient based on the deviation during the radiotherapy.

In some embodiments, films inserted in the slots 101 may be self-developing films. The size of the film inserted into each slot 101 may be matched with the size of the slot 101 without shaking. That is, the size of a film inserted in the first slot 1011 may be matched with the size of the first slot 1011, and the size of a film inserted in the second slot 1012 may be matched with the size of the second slot 1012. Alternatively, the shape of the film may be also matched with an overall shape formed by the first slot 1011 and the second slot 1012. For example, the film may be a film composed of two sub-films that are perpendicular to and intersected with each other, thereby improving the reliability in verifying the deviation between the isocenter of treatment and the isocenter of mechanical rotation.

In some embodiments, as shown in FIG. 2, the extraction groove A may be disposed, on the first outer surface M1, at an intersection point of the first slot 1011 and the second slot 1012. For example, in a case that the intersection point of the first slot 1011 and the second slot 1012 is disposed at a center of the first outer surface M1, the extraction groove A may be disposed at the center of the first outer surface M1.

In some embodiments, as shown in FIG. 2, a cross section of the extraction groove A may be circular. Alternatively, the cross section of the extraction groove A may be in other shapes, such as a rectangle or a triangle. The cross section is a plane parallel to the first outer surface M1.

Figure 3:
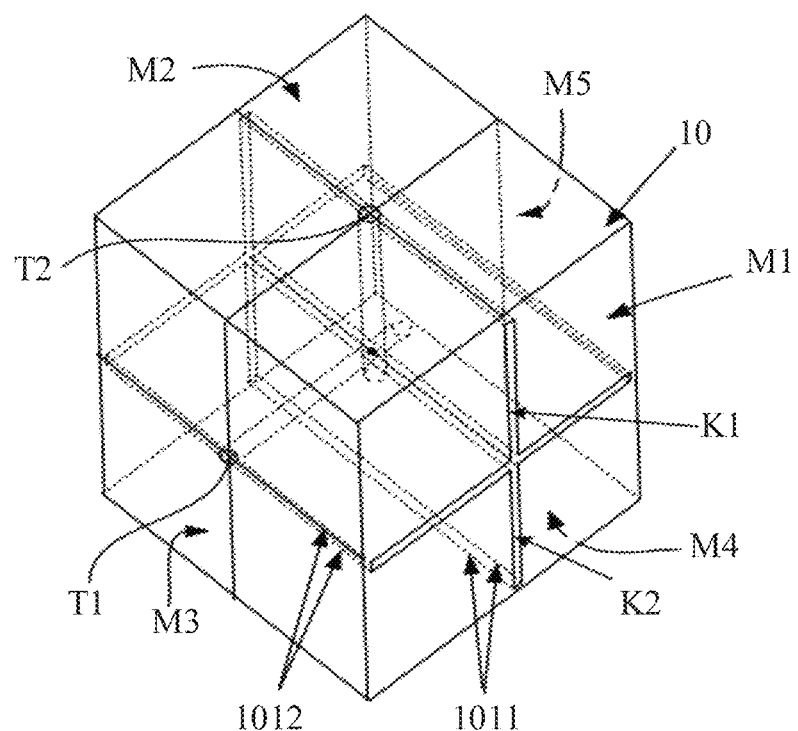
FIG. 3 is a schematic structural diagram of another verification phantom according to an embodiment of the present disclosure.

FIG. 3 is a schematic structural diagram of another verification phantom according to an embodiment of the present disclosure. As shown in FIG. 3, from a position facing the first outer surface M1 of the verification phantom 10, an upper side surface of the verification phantom 10 is a second outer surface M2; a left side surface of the verification phantom 10 is a third outer surface M3; a lower bottom surface of the verification phantom 10 is a fourth outer surface M4; and a right side surface of the verification phantom 10 is a fifth outer surface M5. The verification phantom 10 may be further provided with a first pinhole T1 for communicating an outer surface (for example, the third outer surface M3 or the fifth outer surface M5) of the verification phantom 10 with the first slot 1011, and a second pinhole T2 for communicating an outer surface (for example, the second outer surface M2 or the fourth outer surface M4) of the verification phantom 10 with the second slot 1012.

By the provision of the first pinhole T1 and the second pinhole T2, a needle or a colored pen core may be used first during deviation verification to pass through the first pinhole T1 and make a mark at a center of a film inserted in the first slot 1011, and to pass through the second pinhole T2 and make a mark at a center of a film inserted in the second slot 1012. Then, the two films are irradiated by the radiation source in the image capture component to form focal spots which are then analyzed by the scanner to obtain images with the focal spots. Here, since the center point of the verification phantom 10 is theoretically in coincidence with the isocenter of mechanical rotation, the marks may be used as marks of the mechanical isocenter. Furthermore, it is convenient for the control host to subsequently determine a deviation between the mechanical isocenter and the isocenter of treatment, thereby improving the precision and efficiency in determining the deviation.

In some embodiments, an extending direction of the first pinhole T1 is intersected with the insertion surface of the first slot 1011, and an intersection point of the first pinhole T1 and the insertion surface of the first slot 1011 is the center point of the insertion surface of the first slot 1011. An extending direction of the second pinhole T2 is intersected with the insertion surface of the second slot 1012, and an intersection point of the second pinhole T2 and the insertion surface of the second slot 1012 is the center point of the insertion surface of the second slot 1012. In this way, a pin position, formed through the first pinhole T1, on a radiochromic film inserted in the first slot 1011 is the same as that a pin position, formed through the second pinhole T2, on a radiochromic film inserted in the second slot 1012, thereby further improving accuracy of calculating spatial coordinates of a nuclear physical isocenter based on focal spots on the radiochromic films respectively inserted in the first slot 1011 and the second slot 1012.

Figure 4:
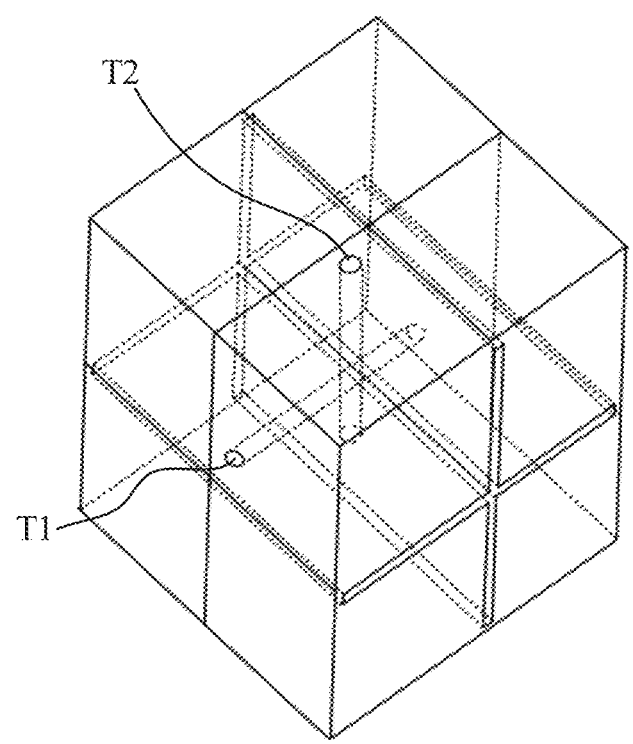
FIG. 4 is a schematic structural diagram of another verification phantom according to an embodiment of the present disclosure.

In some embodiments, as shown in FIG. 4, an intersection point by which the first pinhole T1 is perpendicularly intersected with the second pinhole T2 deviates from the geometric center of the verification phantom 10. In other words, the intersection point by which the first pinhole T1 is perpendicularly intersected with the second pinhole T2 is not in coincidence with the geometric center of the verification phantom 10. For example, the intersection point deviates from the geometric center by a preset distance in a preset direction. Since both the preset direction and the preset distance are known parameters, when the radiochromic films are pinned to determine a reference position, the preset direction and the preset distance may be added in advance for position pre-calculation and correction; and then verification is performed based on a reference position acquired after calculation and correction, such that the precision and efficiency of the verification can be guaranteed. In addition, disposing of the first pinhole T1 and the second pinhole T2 is more flexible, that is, positions of the first pinhole T1 and the second pinhole T2 can be conveniently adjusted and designed based on an actual shape and structure of the verification phantom and a position of another verification module.

In some embodiments, the first pinhole T1 and/or the second pinhole T2 may be through hole(s) that penetrate from one side surface of the verification phantom 10 to an opposite side surface the verification phantom 10. In this way, when making a mark via pinning, an operator can flexibly select a position to make a mark on the radiochromic film.

In some embodiments, when the verification phantom 10 in this embodiment of the present disclosure is further provided with another verification structure, such as a geometric calibration structure or an isocenter verification structure, to make verification structures avoid each other on the verification phantom 10 to prevent impact on verification accuracy of each verification structure, the intersection line, in the verification phantom 10, by which the first slot 1011 is perpendicularly intersected with the second slot 1012 may not pass the geometric center of the verification phantom 10, that is, the intersection line, in the verification phantom 10, by which the first slot 1011 is perpendicularly intersected with the second slot 1012 deviates from the geometric center of the verification phantom 10, thereby making the verification structures avoid each other.

Figure 5:
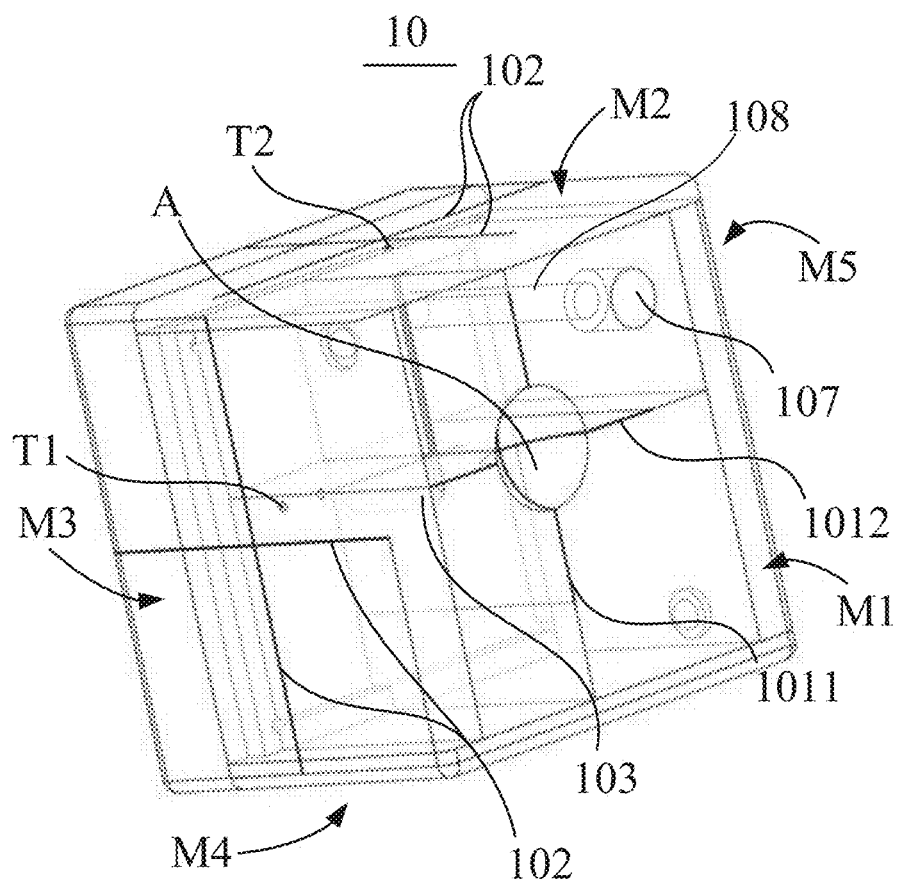
FIG. 5 is a schematic structural diagram of another verification phantom according to an embodiment of the present disclosure.

For example, as shown in FIG. 5, the insertion surface of the first slot 1011 is parallel to the third outer surface M3 and the fifth outer surface M5 of the verification phantom 10; a distance from the insertion surface of the first slot 1011 to the third outer surface M3 is less than or equal to a distance from the insertion surface of the first slot 1011 to the fifth outer surface M5; the insertion surface of the second slot 1012 is parallel to the second outer surface M2 and the fourth outer surface M4 of the verification phantom 10; a distance from the insertion surface of the second slot 1012 to the second outer surface M2 is less than or equal to a distance from the insertion surface of the second slot 1012 to the fourth outer surface M4; and the distance from the insertion surface of the second slot 1012 to the second outer surface M2 is equal to the distance from the insertion surface of the first slot 1011 to the third outer surface M3.

Based on this, the first pinhole T1 penetrates from the third outer surface M3 of the verification phantom 10; and the second pinhole T2 penetrates from the second outer surface M2 of the verification phantom 10. In one aspect, when pinning is performed on films respectively through the first pinhole T1 and the second pinhole T2 to make marks, pinning depths can be as small as possible. In another aspect, the pinning depths of the first pinhole T1 and the second pinhole T2 can be equal to each other. Therefore, the operation is convenient, and errors in the operation of making a mark can be reduced as far as possible.

In some embodiments, as shown in FIG. 5, cross-shaped dash lines 102 are formed on a surface of the verification phantom 10.

The cross-shaped dash lines 102 are formed on at least three surfaces (for example, the second outer surface M2, the third outer surface M3, and the fifth outer surface M5) of the verification phantom 10. The cross center of the cross-shaped dash lines 102 on each surface is set to the position of a target point of the side surface. In this way, the position of the verification phantom 10 can be adjusted, thereby making cross-shaped dash lines 102 on each side surface be in coincidence with cross-shaped laser rays emitted by a laser light, thereby realizing positioning of the verification phantom.

In some embodiments, the cross-shaped dash lines 102 formed on the surface of the verification phantom 10 may be red cross-shaped dash lines, white cross-shaped dash lines, or black cross-shaped dash lines that are displayed on the surface of the verification phantom 10 relatively clearly, thereby facilitating the operation of aligning the cross-shaped rays emitted by the laser light with the red cross-shaped dash lines, white cross-shaped dash lines, or black cross-shaped dash lines.

Since the verification phantom in the related art has a single function and can only verify whether the isocenter of mechanical rotation is in coincidence with the isocenter of a device.

As shown in FIG. 5, in a case that the intersection line by which the first slot 1011 is perpendicularly intersected with the second slot 1012 deviates from a geometric center of the verification phantom, a first marker 103 is disposed at the geometric center of the verification phantom 10. In this way, the mechanical isocenter of a radiotherapy equipment can be calibrated by using the first marker 103; and after the mechanical isocenter is calibrated, geometric calibration may be further performed on an IGRT system, for example, calibrating offsets of a flat panel and a bulb tube, a distance from the bulb tube to the flat panel, a distance from the bulb tube to a rotating shaft, or the like.

In some embodiments, the verification phantom 10 may be a regular hexahedron, namely, a cube structure, that is, each surface of the verification phantom 10 is square. In this way, the overall structure design of the verification phantom is facilitated; and distances from the first marker 103 to all surfaces of the regular hexahedron are all equal to each other. Therefore, geometric parameters of the radiotherapy equipment can be detected more accurately in a three-dimensional space; detected installation errors can be accurately corrected; and the precision in image-guided positioning can be improved.

Figure 6:
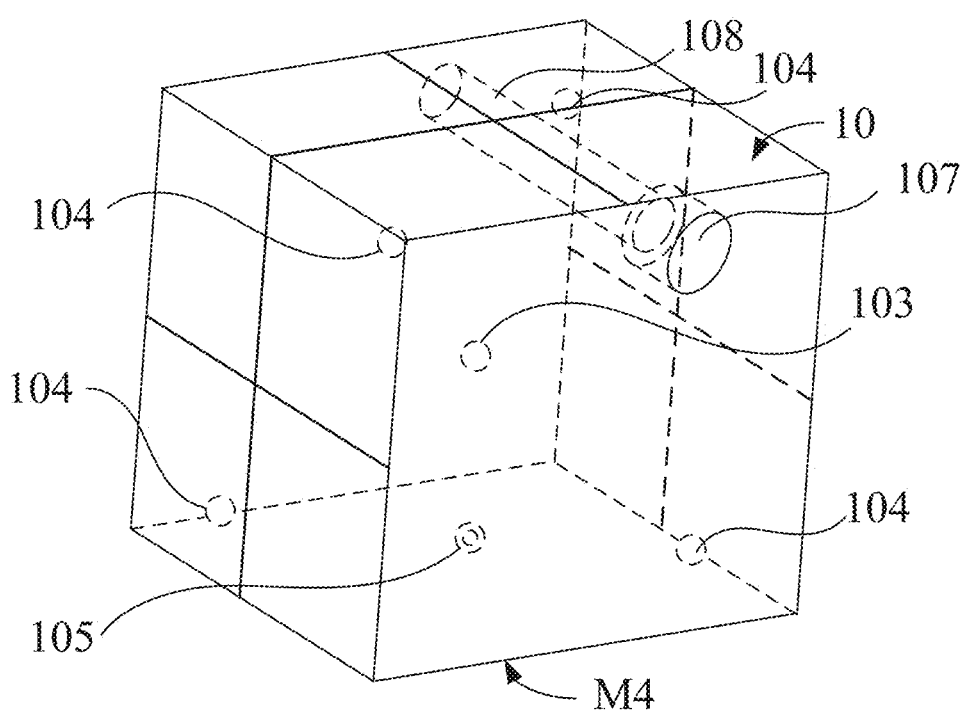
FIG. 6 is a schematic structural diagram of another verification phantom according to an embodiment of the present disclosure.

In some embodiments, as shown in FIG. 6, the verification phantom 10 is further provided with a second marker 104, and the second marker 104 deviates from the geometric center of the verification phantom 10.

In some embodiments, as shown in FIG. 6, at least three second markers 104 are present. There are four second markers in FIG. 6. At least three second markers 104 are distributed, in the verification phantom 10, at the periphery of a circle taking the first marker 103 as a circle center and having a preset radius. The first marker 103 is non-coplanar with a plane defined by any two second markers 104. Distances between every two second markers 104 are equal to each other.

The verification phantom 10 is a regular hexahedron structure. The first marker 103 is disposed at the geometric center of the verification phantom 10. Distances from all the second markers 104 to the first marker 103 are all equal to each other. The second markers 104 are disposed at different positions at the periphery of the circle taking the first marker 103 as the circle center and having the preset radius. The first marker 103 and any two second markers 104 can define a plane. Planes defined by different second markers 104 are non-coplanar. For example, the at least three second markers 104 may be respectively disposed in directions X, Y. and Z in a three-dimensional coordinate system taking the verification phantom 10 as the center.

It should be noted that, to avoid a bad influence of the first marker 103 and the second marker 104 on radiotherapy, the first marker 103 and the second markers 104 are usually made of a material whose density is approximate to the density of human bones. For example, the material may be at least one of aluminum, Teflon, glass, or ceramics. In addition, to facilitate the identification of setting and imaging, both the first marker 103 and the second marker 104 are globule structures.

In some embodiments, as shown in FIG. 6, the verification phantom 10 is further provided with a hollow marker 105. The hollow marker 105 and the first marker 103 are respectively non-coplanar with planes defined by any two second markers 104.

The interior of a hollow marker 105 is filled with air, and does not need to be filled with another special gas. A beam irradiates the verification phantom in this embodiment of the present disclosure. In an image received by the detector, a position corresponding to the hollow marker 105 is presented as a light spot. Particularly, when the verification phantom 10 is a cube, in a process in which the verification phantom is disposed on a treatment couch for verification, since all surfaces of the verification phantom are not clearly differentiated in appearance, orientations of the surfaces of the verification phantom are usually easy to be confused. For example, the position of the hollow marker 105 may be determined in advance. (The hollow marker 105 is not at the geometric center of the cube. For example, the hollow marker 105 may be disposed on a side near the first outer surface M1 of the verification phantom 10.) Therefore, by determining the position of a light spot in an image received by the detector, positioning directions of the head and bottom of the verification phantom on the treatment couch can be determined accurately and fast.

In addition, the hollow marker 105 and the first marker 103 are respectively non-coplanar with planes defined by any two second markers 104, that is, disposing of the hollow marker 105 in the verification phantom 10 meets requirements of the disposing condition of the second marker 104. Therefore, when the verification phantom is used for geometric calibration, the hollow marker 105 may also be used as the second marker 104 for presenting a deviation in a formed image. A greater quantity of second markers 104 leads to more dimensions for presenting the deviation in the formed image, and richer identification data and registration information for the deviation.

In some embodiments, a strip-shaped marker is fixedly disposed on an edge connected to two adjacent surfaces of the verification phantom 10. For another example, a marking groove is further formed in the first outer surface M1 of the verification phantom 10. The cross section of the marking groove is an axially symmetric figure or a centrally symmetric figure.

A strip-shaped marker is fixedly disposed on a side edge of the verification phantom 10. For example, the strip-shaped marker may be an aluminum strip fixedly bonded on the side edge. A marking groove may also be formed in the first outer surface M1 of the verification phantom 10. The cross section of the marking groove is an axially symmetric figure or a centrally symmetric figure. For example, the marking groove is a rectangular groove, a triangular groove, or the like. Various marking structures are disposed on the verification phantom 10. When rays irradiate on the verification phantom, and multiple images in multiple angles that are received by the detector and transmitted to the image server are analyzed, the various marking structures can be all presented in the images, thereby enriching information of the verification phantom in this embodiment of the present disclosure for verifying the treatment center point of the radiotherapy equipment and the isocenter of mechanical rotation, and further improving the accuracy of verification.

Figure 7:
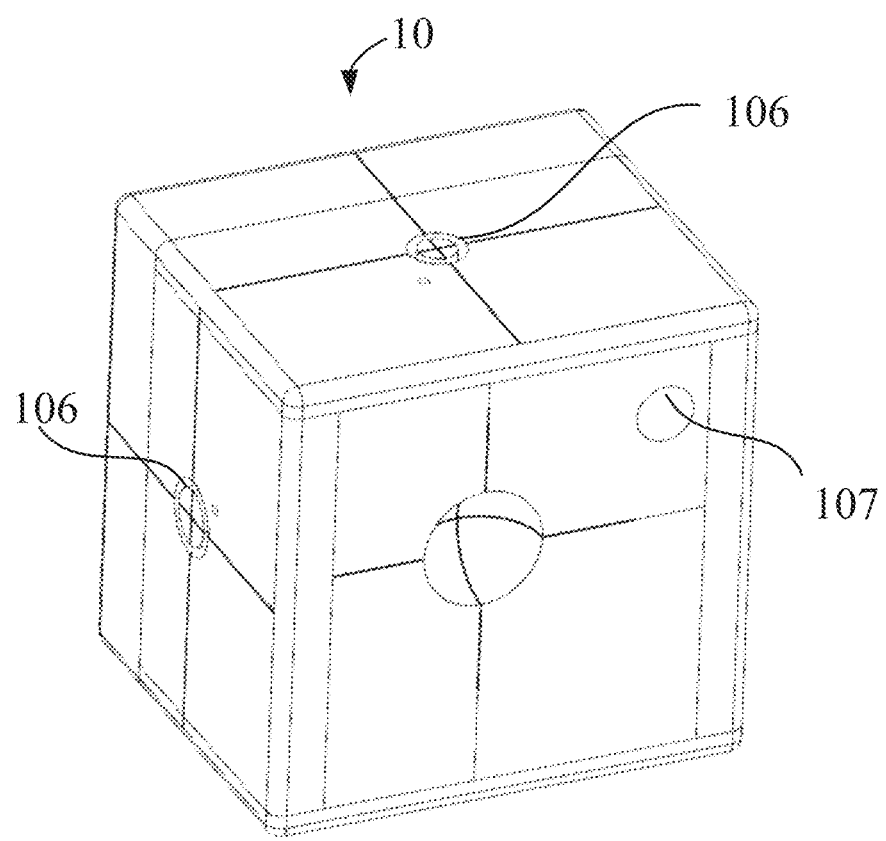
FIG. 7 is a schematic structural diagram of another verification phantom according to an embodiment of the present disclosure.

As shown in FIG. 7, the marking groove may be set to a circular groove 107. The circular grooves formed in four different surfaces (the second outer surface M2, the third outer surface M3, the fourth outer surface M4, and the fifth outer surface M5) of the verification phantom 10 may have different sizes. The upper surface (the second outer surface M2) corresponds to the lower surface (the fourth outer surface M4). The diameter of the circular groove in the upper surface of the verification phantom 10 is less than the diameter of the circular groove in the lower surface of the verification phantom 10. When the circular groove takes the shape of the circular ring shown in FIG. 7, the width and the depth of the circular ring are preset; and the position of the circular groove avoids the positions of the first marker 103, the second marker 104, the hollow marker 105, and the like of the verification phantom 10. In this way, when the verification phantom in this embodiment of the present application is used for geometric calibration, registration information presenting a deviation in a formed image can be enriched; and by disposing circular grooves of different sizes, the direction and the disposing status of the verification phantom can be determined visually during forming of an image. Similarly, the diameter of the circular groove in the left surface (the third outer surface M3) of the verification phantom 10 is less than the diameter of the circular groove in the right surface (the fifth outer surface M5) of the verification phantom 10. When the circular groove takes the shape of the circular ring shown in FIG. 7, the width and the depth of the circular ring are preset; and the position of the circular groove avoids the positions of the first marker 103, the second marker 104, the hollow marker 105, and the like of the verification phantom 10. Therefore, among the six outer side surfaces of the verification phantom 10, two pairs of circular grooves having different sizes are formed in two pairs of opposite side surfaces, and no circular grooves are formed in the other pair of opposite surfaces (the first outer surface M1 and a back surface opposite to the first outer surface M1). Based on these disposing structures, it is convenient for an operator to visually and accurately determine the position and status of the verification phantom in the radiotherapy equipment through the image.

Figure 8:
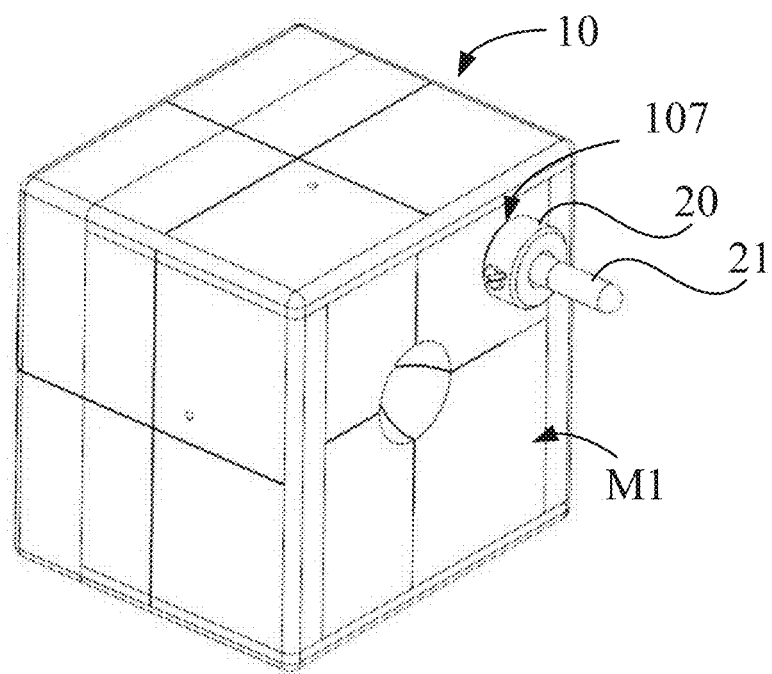
FIG. 8 is a schematic structural diagram of another verification phantom according to an embodiment of the present disclosure.

In some embodiments, the verification phantom in this embodiment of the present disclosure further includes: a first connecting post 20 and/or a second connecting post 30. As shown in FIG. 5, a connecting opening 107 may be formed in the first outer surface M1 of the verification phantom 10. Referring to FIG. 8, the connecting opening 107 may be detachably connected to the first connecting post 20; and an ionization chamber probe 21 may be disposed at an end of the first connecting post 20. Alternatively, referring to FIG. 9, the connecting opening 107 may also be detachably connected to the second connecting post 30; and a tungsten bead 31 may be disposed at an end of the second connecting post 30.

For example, as shown in FIG. 8, the connecting opening 107 formed in the first outer surface M1 of the verification phantom 10 may be detachably connected to the first connecting post 20. The ionization chamber probe 21 disposed at the end of the first connecting post 20 may be configured to detect and verify an amount of rays at a preset position such as a treatment focus position (treatment isocenter), thereby determining whether the amount of rays at the preset position is within a range of required theoretical amounts.

Figure 9:
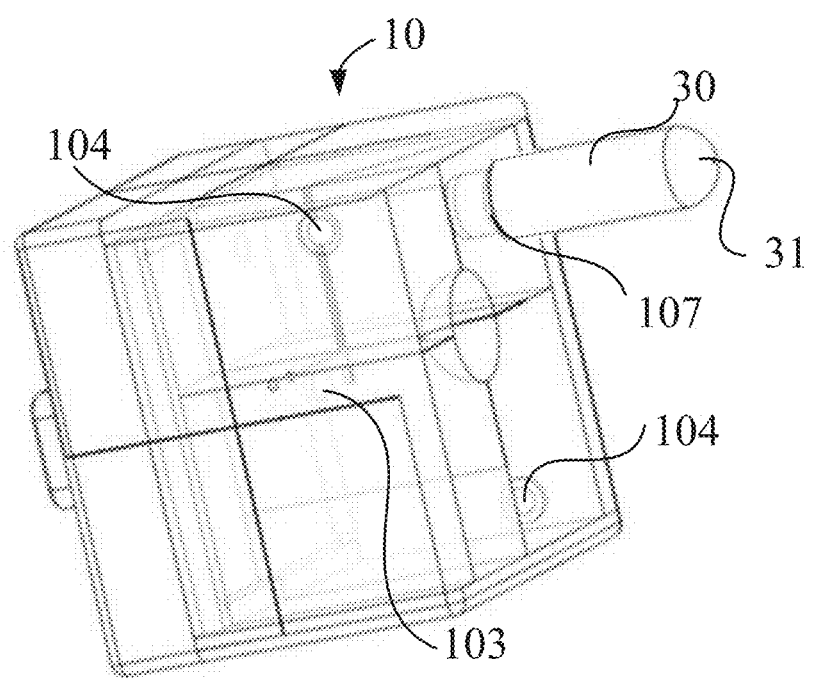
FIG. 9 is a schematic structural diagram of another verification phantom according to an embodiment of the present disclosure.

In some embodiments, as shown in FIG. 9, the connecting opening 107 formed in the first outer surface M1 of the verification phantom 10 may be further detachably connected to the second connecting post 30; and a tungsten bead 31 may be disposed at an end of the second connecting post 30. During usage of the verification phantom in this embodiment of the present application, the tungsten bead 31 may be disposed at the mechanical isocenter. A radiation source is used to irradiate the tungsten bead 31 from different angles. Projection data is acquired from the detector disposed opposite to the radiation source, such as an EPID flat panel or an EPID detector; and an image is generated. The deviation between the mechanical isocenter and the treatment isocenter is verified by analyzing a light spot center and a shadow center in the image acquired by the EPID flat panel or the EPID detector.

In addition, to resolve the problem that the attenuation degrees of rays in different directions are inconsistent during imaging because the thicknesses of solid structures through which the rays in different directions irradiate the tungsten bead 31 are different, the interior of the second connecting post 30 may also be hollow, thereby resolving the problems that the brightness of the image is uneven and that subsequent image analysis is relatively difficult because the attenuation degrees of the rays irradiating the tungsten bead 31 in different directions are inconsistent during imaging.

In some embodiments, an internal thread is formed in an internal periphery wall of the connecting opening 107. External threads are respectively formed on the first connecting post 20 and the second connecting post 30. The first connecting post 20 and the second connecting post 30 are in threaded connection with the connecting opening 107, respectively. The first connecting post 20 or the second connecting post 30 is disposed detachably and replaceably in this fashion, such that the detaching and the installation are relatively convenient; and the firmness and the accuracy of the connection can be guaranteed after the connection.

In some embodiments, as shown in FIG. 5, the verification phantom 10 is further provided with a through channel 108 communicated with the connecting opening 107. The internal diameter of the through channel 108 is less than or equal to the internal diameter of the connecting opening 107. When the internal diameter of the through channel 108 is equal to the internal diameter of the connecting opening 107, the first connecting post 20 or the second connecting post 30 is detachably mounted in the connecting opening 107, that is, the position relationship between the first connecting post 20 or the second connecting post 30 and the verification phantom 10 can be adjusted by using the through channel 108. When the internal diameter of the through channel 108 is less than the internal diameter of the connecting opening 107, the convenience of installation and detaching can be guaranteed; and a connection structure can be mounted in the through channel 108 in time.

It should be noted that, the ionization chamber is a detector that uses the ionization effect of ionizing radiation to measure ionizing radiation, and is also referred to as an ion chamber. The ionization chamber probe 21 needs to be connected to a measurement result display device by using a wire. As the wire is easy to be damaged when being exposed in an environment having a large amount of rays, in order to make detection of an amount of rays be easier to be implemented and disposed on the verification phantom, the through channel 108 may be formed in the verification phantom 10 and the interior of the first connecting post 20 is also hollow. In this way, as shown in FIG. 8, when disposing the ionization chamber probe 21, the ionization chamber probe 21 may be directly fed, through the through channel 108 from the rear of the phantom, into an end of the first connecting post 20 connected to the connecting opening 107, thereby avoiding wire winding in the radiotherapy equipment, and avoiding damage of a wire exposed in an environment having a large amount of rays.

In some embodiments, the verification phantom 10 may be a solid structure. The verification phantom 10 may be a cube, namely, a regular hexahedron. All surfaces of the verification phantom 10 that is a regular hexahedron are square. In this way, the overall structure design of the verification phantom is facilitated. The first slot 1011 and the second slot 1012 are respectively disposed on any two adjacent surfaces of the regular hexahedron, which also facilitates disposing and machining of a structural size.

In some embodiments, the verification phantom 10 may also be a prismoid, such as a cuboid. Alternatively, the verification phantom 10 may be a cylinder. Since the verification phantom 10 having a cuboid structure or a cylinder structure has a definite length-to-width relationship, in addition to application of the verification function of the verification phantom, directions of the head and bottom of the treatment couch may also be identified conveniently based on the length direction of the cuboid or cylinder.

In some embodiments, the verification phantom 10 may also be a sphere; and the surface of the sphere is arc-shaped, such that the first slot 1011 and the second slot 1012 can be disposed more flexibly. The shape of the verification phantom 10 is not limited in this embodiment of the present disclosure.

In some embodiments, the verification phantom 10 is made of an organic glass material. For example, the verification phantom 10 is made of a black organic glass material; or the verification phantom 10 is made of a transparent organic glass material.

When the verification phantom 10 is made of an organic glass material that has relatively high permeability for both laser rays and a beam emitted by the radiation source, transmission and imaging of the laser rays and the beam emitted by the radiation source cannot be impacted. For example, the verification phantom 10 may be made of a black organic glass material or a transparent organic glass material. The verification phantom 10 made of the transparent organic glass material is transparent, such that structures such as the first marker 103, the second marker 104, the first slot 1011, and the second slot 1012 in the verification phantom 10 can be seen visually, to facilitate disposing of the verification phantom during use.

Figure 10:
FIG. 10 is a schematic diagram of the connection of a verification phantom according to an embodiment of the present disclosure.

In some embodiments, as shown in FIG. 10, a connecting rack 40 for connecting the treatment couch is connected to the verification phantom 10.

Based on this, the connecting rack 40 may be set to a rotary installation structure, such that a relationship between the verification phantom 10 and the treatment couch or another installation position can be rotationally adjusted by adjusting the connecting rack 40. The adjusting angle may be set within 45 degrees.

Different radiotherapy equipment have different device structures and disposing requirements for verification phantoms. To ensure that the verification phantom can be fixed on the radiotherapy equipment and that the verification phantom can be mounted in different radiotherapy equipment in a matching fashion as adaptive as possible, the connecting rack 40 is connected to a side surface, distal from the first outer surface M1, of the verification phantom 10; and the verification phantom 10 is connected to the treatment couch of the radiotherapy equipment through the connecting rack 40.

The following still uses a gamma knife as an example. When the verification phantom in this embodiment of the present application is applied to a head gamma knife, a U-shaped rack at a fixing position of the treatment couch of the head gamma knife is connected to the connecting rack 40, thereby fixing the verification phantom in this embodiment of the present disclosure to the treatment couch of the head gamma knife. When the verification phantom in this embodiment of the present application is applied to a body gamma knife, a base plate is connected to the connecting rack 40; and the verification phantom in this embodiment of the present application is horizontally disposed on a treatment couch through the base plate. In this way, by disposing the connecting rack 40, on the premise that the verification phantom in this embodiment of the present application cannot be damaged or impacted, the verification phantom in this embodiment of the present application can be applied to verification, registration, and positioning of various radiotherapy equipment; and universality of the verification phantom in this embodiment of the present application to radiotherapy equipment of different types, models, treatment positions can be improved.

An embodiment of the present disclosure further provides a radiotherapy system. The radiotherapy system may include: the verification phantom illustrated in any one of FIGS. 1 to 10 and radiotherapy equipment.

In some embodiments, the radiotherapy equipment may include a radiation source and a treatment couch. Based on this, the radiotherapy equipment may further include an image capture component. The image capture component includes a detector disposed opposite to the radiation source, and/or an imaging apparatus (including a bulb tube and a flat panel detector disposed opposite to the bulb tube). The radiotherapy system may further include a control host, an image server, a scanner, and three laser lights.

The verification phantom may be disposed on the treatment couch; the image capture component may be connected to the image server; the image server may be connected to the control host; and the control host may be connected to the treatment couch. Alternatively, the image server may be directly integrated in the control host. The radiation source may be a radiation source of a treatment head in the radiotherapy equipment, that is, rays emitted by the radiation source may also be configured to irradiate a target point on a patient, so as to perform radiotherapy on the patient.

In an embodiment of the present disclosure, the scanner may be configured to scan a film, irradiated by the radiation source, in the verification phantom to develop a focal spot formed on the film, and a therapist may send an image containing the focal spot to the image server. The image capture component and the radiation source may be configured to capture images of the verification phantom and send the captured images to the image server. The image server may be configured to analyze the acquired images and determine a deviation (such as a deviation between the isocenter of treatment and the isocenter of mechanical rotation) based on an analysis result; and the image server may further send the determined deviation to the control host. The control host may be configured to adjust the position of the treatment couch based on the received deviation, and may store the deviation. Each laser light may be configured to emit rays to the verification phantom. In some embodiments, the rays emitted from the laser light may be cross-shaped rays.

In some embodiments, the control host may include an upper computer and a lower computer; the upper computer may be connected to the lower computer; and the lower computer may be connected to other parts (such as the treatment couch and the image capture component) in the radiotherapy system. The upper computer may be configured to send a control instruction to the lower computer; and the lower computer may control working statuses of other parts based on the received control instruction.

In summary, the embodiments of the present disclosure provide a radiotherapy system which includes a verification phantom. The radiation source in the radiotherapy equipment and the bulb tube in the image capture component may emit rays to the verification phantom; the detector disposed opposite to the radiation source and the detector disposed opposite to the bulb tube may receive the rays and capture images based on the rays; and the detector may send the captured images to the image server. The scanner may scan a film, irradiated by the radiation source, in the verification phantom to develop a focal spot formed on the film, and a therapist may send an image containing the focal spot to the image server. The image server may analyze the acquired images to determine the deviation between the isocenter of treatment and the isocenter of mechanical rotation or to determine the deviation of the isocenter of mechanical rotation, and may send the deviation to the control host, which will precisely position the patient based on the deviation. Therefore, the precision of radiotherapy is improved, and the quality of radiotherapy is guaranteed.

It may be clearly understood by a person skilled in the art that, for the purpose of convenient and brief description, for a detailed working process of the radiotherapy system and the verification phantom of the same as described above, reference may be made to a corresponding process in the forgoing method embodiments, and details are not described herein again.

Described above are merely optional embodiments of the present disclosure, but are not intended to limit the present disclosure. Any modifications, equivalent replacements, improvements and the like made within the spirit and principles of the present disclosure shall fall within the protection scope of the present disclosure.

What is claimed is:

1. A verification phantom, provided with a slot for holding a film, wherein the slot comprises a first slot and a second slot; an opening of the first slot and an opening of the second slot are both disposed on a first outer surface of the verification phantom; and an extraction groove is disposed at a junction, on the first outer surface, of the opening of the first slot and the opening of the second slot.

2. The verification phantom according to claim 1, wherein an intersection point of the opening of the first slot and the opening of the second slot is disposed at a center of the first outer surface; and the extraction groove is disposed at the center of the first outer surface.

3. The verification phantom according to claim 1, wherein an insertion surface of the first slot is perpendicular to an insertion surface of the second slot; and both the first slot and the second slot pass through a center point of the verification phantom.

4. The verification phantom according to claim 1, wherein a cross-section of the extraction groove is circular, rectangular, or triangular.

5. The verification phantom according to claim 1, wherein the verification phantom is provided with a first pinhole for communicating an outer surface of the verification phantom with the first slot and provided with a second pinhole for communicating the outer surface of the verification phantom with the second slot.

6. The verification phantom according to claim 5, wherein:
an extending direction of the first pinhole is intersected with an insertion surface of the first slot; and an intersection point thereof is a center point of the verification phantom; and
an extending direction of the second pinhole is intersected with an insertion surface of the second slot; and an intersection point thereof is the center point of the verification phantom.

7. The verification phantom according to claim 5, wherein the first pinhole is disposed in a side surface of the verification phantom; and the second pinhole is disposed in a top surface of the verification phantom.

8. The verification phantom according to claim 5, wherein an extending direction of the first pinhole is perpendicular to an insertion surface of the first slot; and an extending direction of the second pinhole is perpendicular to an insertion surface of the second slot.

9. The verification phantom according to claim 5, wherein an intersection point by which the first pinhole perpendicularly is intersected with the second pinhole deviates from a geometric center of the verification phantom.

10. The verification phantom according to claim 1, wherein the verification phantom is a cube, a prismoid, a cuboid, a cylinder, or a sphere.

11. The verification phantom according to claim 1, wherein the verification phantom is made of organic glass.

12. The verification phantom according to claim 1, wherein an intersection line by which the first slot perpendicularly is intersected with the second slot deviates from a geometric center of the verification phantom.

13. The verification phantom according to claim 1, wherein the verification phantom further comprises: a first connecting post and/or second connecting post; a connecting opening is disposed in a surface of the verification phantom; the connecting opening may be detachably connected to the first connecting post and/or the second connecting post; the first connecting post is provided with an installation channel for installing an ionization chamber probe; and a tungsten bead is disposed at an end of the second connecting post.

14. The verification phantom according to claim 1, wherein a first marker is disposed at a geometric center of the verification phantom.

15. The verification phantom according to claim 14, wherein the verification phantom is further provided with at least one second marker that deviates from the geometric center of the verification phantom.

16. The verification phantom according to claim 15, wherein the verification phantom is further provided with a through channel communicated with the connecting opening.

17. The verification phantom according to claim 15, wherein at least three second markers are present and are distributed, in the verification phantom, at a periphery of a circle taking the first marker as a circle center and having a preset radius; and the first marker is non-coplanar with a plane defined by any two second markers.

18. The verification phantom according to claim 15, wherein the verification phantom is further provided with a hollow marker; and the hollow marker and the first marker are both non-coplanar with a plane defined by any two second markers.

19. The verification phantom according to claim 1, wherein a marking groove is further formed in at least one surface of the verification phantom.

20. The verification phantom according to claim 1, wherein a connecting rack for connecting a treatment couch is connected to the verification phantom.

* * * * *